US006659956B2

(12) United States Patent
Barzell et al.

(10) Patent No.: US 6,659,956 B2
(45) Date of Patent: Dec. 9, 2003

(54) MEDICAL INSTRUMENT POSITIONER

(75) Inventors: Winston E. Barzell, Sarasota, FL (US); Willet F. Whitmore, III, Sarasota, FL (US); Stephen E. Brauner, Bradenton, FL (US); Roger F. Wilson, Sarasota, FL (US); Salvatore A. Uccello, Sarasota, FL (US)

(73) Assignee: Barzell-Whitmore Maroon Bells, Inc., Sarasota, FL (US)

( * ) Notice: Subject to any disclaimer, the term of this patent is extended or adjusted under 35 U.S.C. 154(b) by 0 days.

(21) Appl. No.: 09/893,984

(22) Filed: Jun. 29, 2001

(65) Prior Publication Data

US 2003/0014039 A1 Jan. 16, 2003

(51) Int. Cl.$^7$ ................................................ A61B 8/00
(52) U.S. Cl. ...................................................... 600/461
(58) Field of Search ................................. 600/439, 562, 600/461, 7, 459, 462; 604/155, 154; 607/128; 128/DIG. 12, DIG. 1

(56) References Cited

U.S. PATENT DOCUMENTS

| | | | | |
|---|---|---|---|---|
| 4,742,829 A | | 5/1988 | Law et al. .................. 128/660 |
| 4,767,406 A | * | 8/1988 | Wadham et al. ............ 604/155 |
| 5,178,148 A | | 1/1993 | Lacoste et al. ........ 128/660.03 |
| 5,244,461 A | * | 9/1993 | Derlien ........................ 604/65 |
| 5,398,690 A | | 3/1995 | Batten et al. .......... 128/662.05 |
| 5,474,071 A | | 12/1995 | Chapelon et al. ...... 128/660.03 |
| 5,494,039 A | | 2/1996 | Onik et al. ............ 128/662.05 |
| 5,592,942 A | * | 1/1997 | Webler et al. ............... 600/445 |
| 5,931,786 A | * | 8/1999 | Whitmore et al. .......... 600/459 |
| 5,938,583 A | * | 8/1999 | Grimm ........................ 600/1 |
| 6,007,474 A | * | 12/1999 | Rydell ........................ 600/7 |
| 6,206,832 B1 | * | 3/2001 | Downey et al. ............ 600/439 |
| 6,292,681 B1 | * | 9/2001 | Moore ........................ 600/407 |

OTHER PUBLICATIONS

B & K User Gude for the stepping Unit UA 1084, Oct. 1994, 6 pages.
"Martin" Immobilization Device, Catalog #9102–MA, Mick Radio–Nuclear Instruments, Inc., 2 pages.
Northwest Transperinel Prostate Implant Stabilization Device, Transperineal Prostate Implant Dosimetry Service, 2 pages.
"Cotan" Stabilizing Device, Catalog #8812–C, Mick Radio–Nuclear Instruments, Inc., 2 pages.
Portable Stabilizers, Hutchinson Medical Designs, 1 page.
"Ultrasound Transducer Covers and Needle Guides", brochure of Civco Medical Instruments, Kalona, Iowa 52247, 8 pages.
"Brachytherapy Ultrasound system", brochure of Carolina Medical Inc., King, NC 270121–0307, 2 pages.

* cited by examiner

Primary Examiner—Francis J. Jaworski
Assistant Examiner—Maulin Patel
(74) Attorney, Agent, or Firm—Pennie & Edmonds LLP

(57) ABSTRACT

The present invention relates to a medical instrument positioning device for controlled placement of a wide variety of medical instruments, such as an ultrasound transducer probe. The positioning device comprises a base member and a central shaft operatively associated with the base, a carriage member having a cavity configured and dimensioned to receive at least a portion of a medical instrument and slideably connected to the central shaft, a drive member coupled to the carriage member and engageable with the central shaft for movement with the central shaft and disengagement from the central shaft for sliding movement along the central shaft, and a quick release member operatively associated with the drive member. The quick release member has an inactive configuration in which the drive member engages the central shaft and an active configuration in which the drive member disengages the central shaft.

23 Claims, 7 Drawing Sheets

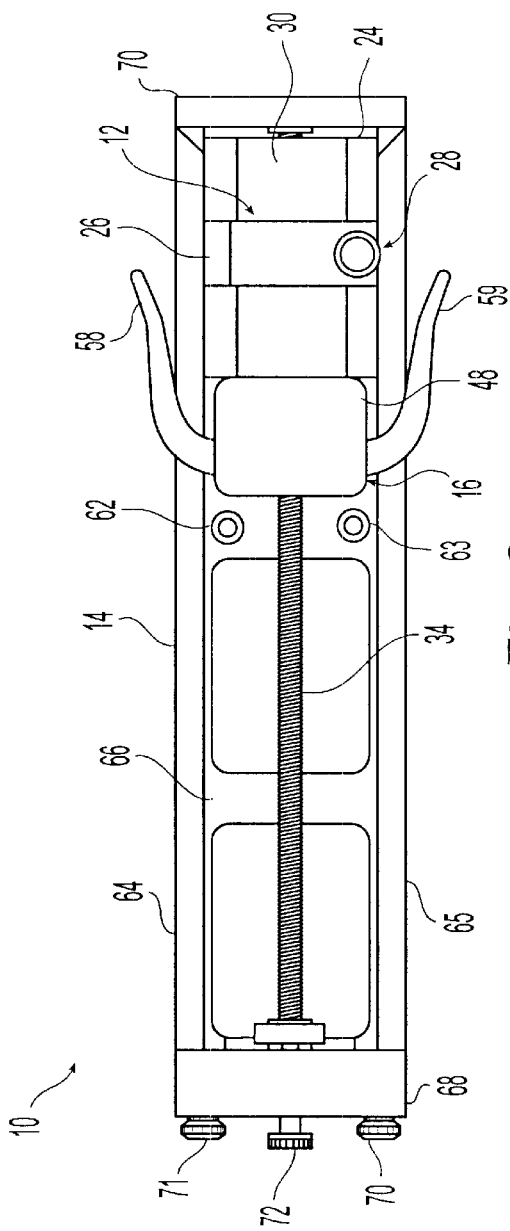
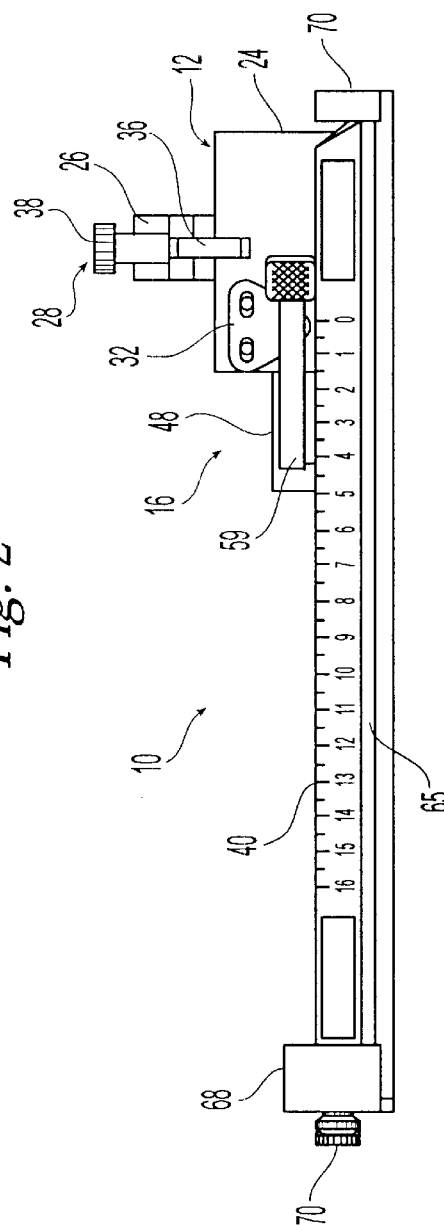

MEDICAL INSTRUMENT POSITIONER

FIELD OF THE INVENTION

This invention relates generally to a device for positioning a medical instrument, and more particularly to an adjustable support and positioning device for an ultrasound imaging probe.

BACKGROUND ART

There are a number of medical procedures that utilize ultrasound images for diagnostic and/or therapeutic purposes. For example, one widely applied minimally invasive procedure for the treatment of prostate cancer is the percutaneous transperineal implantation of radioactive seeds called brachytherapy. This procedure is performed with the patient in the lithotomy position, using an ultrasound imaging probe placed in the rectum to monitor seed placement. Precise and reproducible orientation and positioning of the ultrasound imaging probe in the rectum is a key element in both the calculations required for determining the number and distribution of radioactive seeds required for treatment and their subsequent placement using pre-loaded needles guided by a perineal template and real time ultrasound imaging.

Another form of treatment that is promising is cryotherapy. This procedure is performed with the patient in the lithotomy position, using an ultrasound imaging probe placed in the rectum to guide an instrument called a cryoprobe and to monitor the freezing of the gland. Typically, in cryotherapy, liquid nitrogen or a similar freezing agent is circulated through the cryoprobe, which is placed in contact with the tumor. The tumor is frozen as is some of the surrounding tissue. Often, the treatments are cyclic in which the tumor is frozen, allowed to thaw, and then refrozen. The goal of this treatment is to rapidly kill the cancer cells without subjecting the surrounding healthy tissue to trauma.

In the field of general surgery, there is a need for detailed visualization of the anatomy of the distal rectum and anus in patients with rectal cancer. High resolution ultrasound imaging of this area has been shown to be of great value in determining whether the cancer extends into the pelvic floor structures. This information is used by the surgeon to decide whether the anal continence mechanism may be saved or whether a colostomy will be required. The use of two dimensional images to construct a three dimensional view for study is considered the state of the art for evaluating these patients.

As these examples illustrate, multiple sequential two dimensional, transverse or radial, high resolution ultrasound images of the human pelvis, distal colon, and rectum are very useful and can be obtained by appropriate use of transrectal ultrasound transducers. In an analogous fashion, multiple sequential two dimensional, high resolution images of other anatomical regions can be obtained using known medical imaging instrumentation. Computer algorithms have been developed that use these images to construct a clinically valuable three dimensional holographic view of the anatomical region of interest. In order to optimize the resolution and accuracy of the generated three dimensional images, accurate sequencing and accurate spacing of the two dimensional image acquisition is essential.

Although manual withdrawal of the imager, such as a transrectal ultrasound transducer, can achieve proper image sequencing, it is a poor method for obtaining accurate image spacing. Presently, there are many homemade and commercially available devices for mounting, positioning and rotating the various commercially available imagers. None of these devices have achieved wide acclaim because of significant limitations in their ease of use and level of precision of probe control and placement.

Mechanized positioners for the imaging tranducers do exist. However, many lack the ability to disengage the motor or other mechanism used to position the imager. Thus, manual positioning of the imager for rapid placement and repeat scans is not possible. Additionally, the risk of accidental patient injury from motor driven insertion exists. Risk of patient injury also exists because of the lack of tactile and other feedback provided by manual movement of the imaging transducers in other mechanized positioners.

Thus, there is a need for an improved medical instrument positioning device.

SUMMARY OF THE INVENTION

The present invention relates to a medical instrument positioning device for controlled placement of a wide variety of medical instruments, such as an ultrasound transducer probe. The positioning device comprises a base member having a base and a central shaft operatively associated with the base, a carriage member having a cavity configured and dimensioned to receive at least a portion of a medical instrument and slideably connected to the central shaft, a drive member coupled to the carriage member and engageable with the central shaft for movement with the central shaft and disengageable from the central shaft for sliding movement along the central shaft, and a quick release member operatively associated with the drive member. The quick release member has an inactive configuration in which the drive member engages the central shaft and an active configuration in which the drive member disengages the central shaft.

In one embodiment, the base includes first and second crossbars and first and second elongated, spaced parallel side rails, with the first and second side rails parallel with the central shaft. The central shaft can be threaded and rotatably connected at first and second ends thereof to the first and second crossbars so that rotation of the central shaft with the quick release member in the inactive configuration causes incremental movement of the drive member along the central shaft. In order to provide smooth movement, at least one of the drive member and carriage member can include first and second flanges extending therefrom and the first and second side rails each include a slot for slideably receiving one of the flanges. The drive member can have an engagement member that receives at least a portion of the release lever so that upon actuation of the release member, the engagement member either engages or disengages the central shaft.

In one embodiment, the base is provided with a coupler for connection to a support stand. Furthermore, the carriage member can have a probe securing member to support the medical instrument and a fastener so that the probe securing member and fastener secure the medical instrument in the cavity of the carriage member. The base member can also include at least one scale to provide indicia of displacement of the carriage member along the base member. The scale can cooperate with a carriage scale marker on the carriage member to indicate the numerical position of the carriage member on the base member. In order to couple the device to a motor, the base member can be provided with a rotatable motor engagement member attached at a first end to the central shaft and removably coupled to a motor at a second end. If an electric motor is used, at least a portion of the motor engagement member can be made of a non-conductive material to electrically isolate the motor and the device.

In order to provide some limit on the force used to move the medical instrument, the device can include a safety release element that uncouples the drive member from the carriage member when a movement force on the carriage member exceeds a threshold value. In one embodiment, the safety release element comprises a magnet on the carriage member and a magnet on the drive member. The magnets magnetically couple the drive member and the carriage member. The magnetic field of one of the magnets (either on the carriage member or drive member) can be adjustable to adjust the threshold value. This can be achieved, for example, by making the adjustable magnet movable with respect to the other magnet to thereby adjust the threshold value. A set screw can be used to move the adjustable magnet.

In another embodiment, the medical instrument positioning device comprises a base member having a base and a central shaft operatively associated with the base, a carriage member having a cavity configured and dimensioned to receive at least a portion of a medical instrument and slideably connected to the central shaft, a drive member removably coupled to the carriage member and engageable with the central shaft for movement along the central shaft, and a safety release element that uncouples the drive member from the carriage member when a movement force on the carriage member exceeds a threshold value. In this embodiment, the safety release element can include a first plurality of magnets on the carriage member and a second plurality of magnets on the drive member. The first and second plurality of magnets magnetically couple the drive member and the carriage member. The magnetic fields of at least some of the first and second plurality of magnets can be adjustable to adjust the threshold value.

BRIEF DESCRIPTION OF THE DRAWINGS

The present invention is described in detail below with reference to the drawings in which:

FIG. 2 is a top view of the device of FIG. 1.

FIG. 3 is a side view of the device of FIG. 1.

DETAILED DESCRIPTION OF THE INVENTION

In the description which follows, any reference to either direction or orientation is intended primarily and solely for purposes of illustration and is not intended in any way as a limitation to the scope of the present invention. Also, the particular embodiments described herein, although being preferred, are not to be considered as limiting of the present invention.

Figure 1:
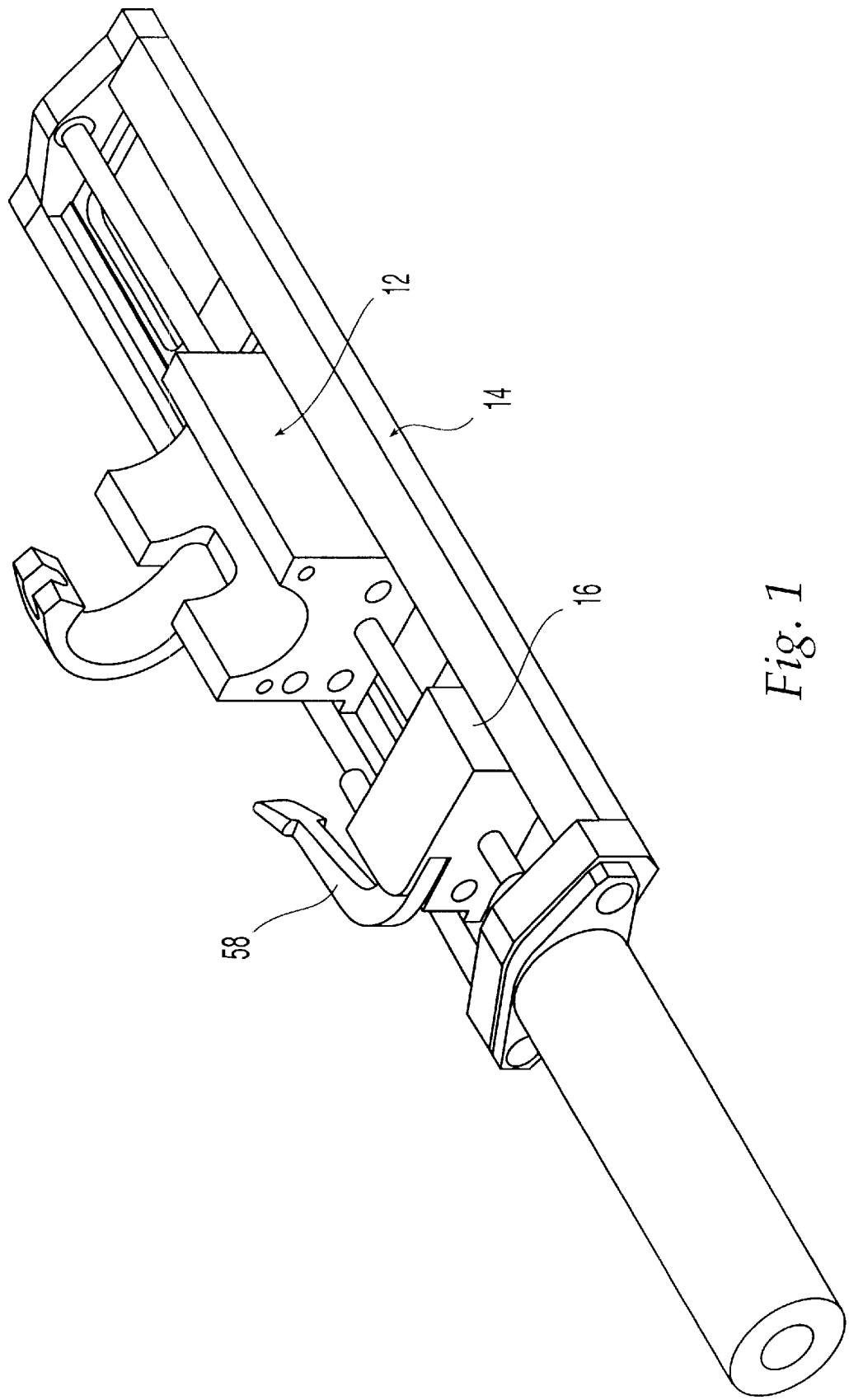
FIG. 1 is a perspective view of one embodiment of the medical instrument positioning device according to the present invention.

As shown in FIG. 1, device 10 of the present invention includes carriage member 12, base member 14, and drive member 16. As shown, carriage member 12 and drive member 16 are separate components. However, carriage member 12 and drive member 16 could be integral. Carriage member 12 is adapted to receive and securely clamp around a central enlarged portion of a medical instrument, such as an ultrasound transducer probe. For simplicity, the medical instrument will be referred to as "the probe". Although carriage member 12 is adapted to securely clamp the probe in the mount, the holding mechanism can be selected such that the probe can be manually rotated when it is in place but not securely fastened in carriage member 12. Carriage member 12 is adapted for slidable longitudinal movement along base member 14. Drive member 16 is coupled to carriage member 12 and drive member 16 is adapted for longitudinal movement along the base member 14.

All of the components of the present device 10 can be made from materials commonly found in medical instruments. In one embodiment, device 10 is made from a metal and is machined. Alternatively, many of the components can be fabricated or cast of a plastic, with engineering thermoplastics, such as DELRIN, being exemplary. Nylons, polycarbonates and like materials can be used, if desired. Additionally, non-conductive materials, such as plastics or ceramics, may also be used.

With more specific detail of the components of the invention 10 discussed herebelow, and referring additionally to FIGS. 2–6, carriage member 12 (with the probe not shown) is longitudinally slideable along base member 14. In an exemplary embodiment, carriage member 12 has two parallel flanges 20 and 21 located at the base of carriage member 12 that slideably fit within base member 14. Located at the outer side edges within base member 14 are two parallel, opposed, longitudinal slots 30 and 31 (shown in FIG. 8) running along the length of base member 14. Flanges 20 and 21 slideably fit within longitudinal slots 30 and 31 to minimize movement in directions other than along slots 30 and 31. Longitudinal slots 30 and 31 can be treated with some form of lubricant such as silicon to facilitate the sliding movement of flanges 20 and 21 in longitudinal slots 30 and 31. In one embodiment, carriage member 12 also has central bore 22 which is substantially cylindrical and has a first diameter that extends through the length of carriage member 12. Threaded shaft 34, which extends along the length of base member 14 and is located approximately centrally in base member 14, has a smaller second diameter and fits within central bore 22 allowing carriage member 12 to slide along the length of base member 14 longitudinally.

Figure 4:
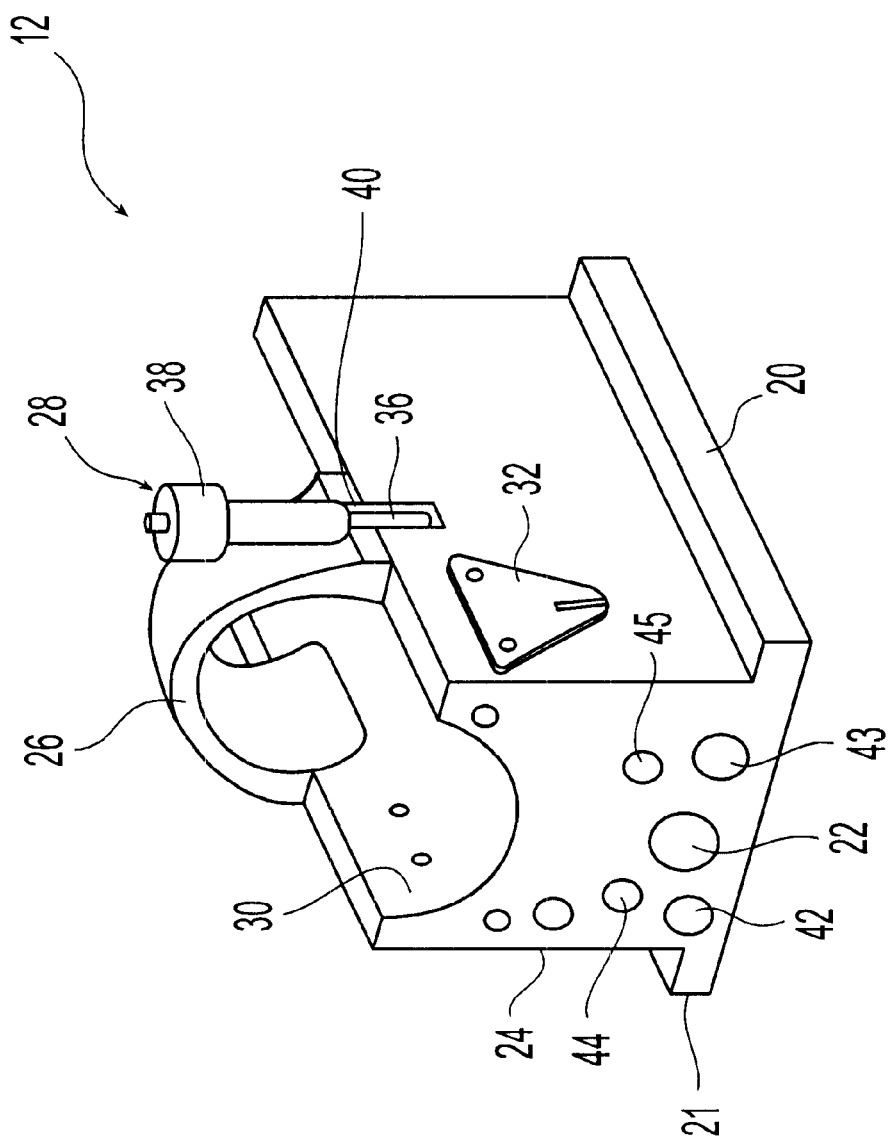
FIG. 4 is a perspective view of one embodiment of the carriage member according to the present invention.

Referring to FIG. 4, carriage member 12 comprises body portion 24 which houses central bore 22. In an exemplary embodiment, located at the base of body portion 24 are flanges 20 and 21 which extend outwardly in the transverse direction from the base of body portion 24 and run along the length of body portion 24. Body portion 24 can include a carriage scale marker plate 32, which in conjunction with a carriage scale marker 40 located on base member 14, indicates the position of carriage member 12. Body portion 24 has a recess or cavity 33 that is configured and dimensioned to receive and support at least a portion of the probe. In an exemplary embodiment, attached to body portion 24 is probe latch 26. Probe latch 26 is shaped to receive the probe, has a notch 40, and is used in cooperation with cavity 33 and fastener 28 to securely hold the probe in place. Fastener 28 can include a threaded fastener shaft 36 that is attached to body portion 24 and a textured cap 38 that is threaded internally and fits over threaded fastener shaft 36.

In order to secure the probe in carriage member 12, fastener 28 is first disengaged from probe latch 26. Fastener 28 is disengaged by being moved from a first locked position (shown in FIG. 4) to a second unlocked position. In an exemplary embodiment, this is accomplished by rotating textured cap 38 in a counter-clockwise direction thereby shifting textured cap 38 in an upward direction. This upward movement disengages the lower portion of textured cap 38 from notch 40, freeing threaded fastener shaft 36 to pivot about its hinge. Pivoting threaded fastener shaft 36 about its hinge will move fastener 28 from its first locked position to its second unlocked position. Probe latch 26 can now be moved from a first securing position (shown in FIG. 4) to a second unlocked position. In an exemplary embodiment, this is accomplished by pivoting probe latch 26 about its hinge from a first locked position to a second unlocked position, thereby allowing a probe to be placed in cavity 33. Once the probe is placed in cavity 33, probe latch 26 is pivoted from the second unlocked position to the first securing position. At this point, in an exemplary embodiment, while sitting in cavity 33, the probe can be rotated to its desired orientation by the user or physician. Fastener 28 is then moved from the second unlocked position to the first locked position. Textured cap 38 is then rotated clockwise shifting textured cap 38 in a downward direction. As textured cap 38 translates in a downward direction, the bottom portion of textured cap 38 engages notch 40 of probe latch 26 thereby securing the probe or medical instrument in carriage member 12.

Figure 6:
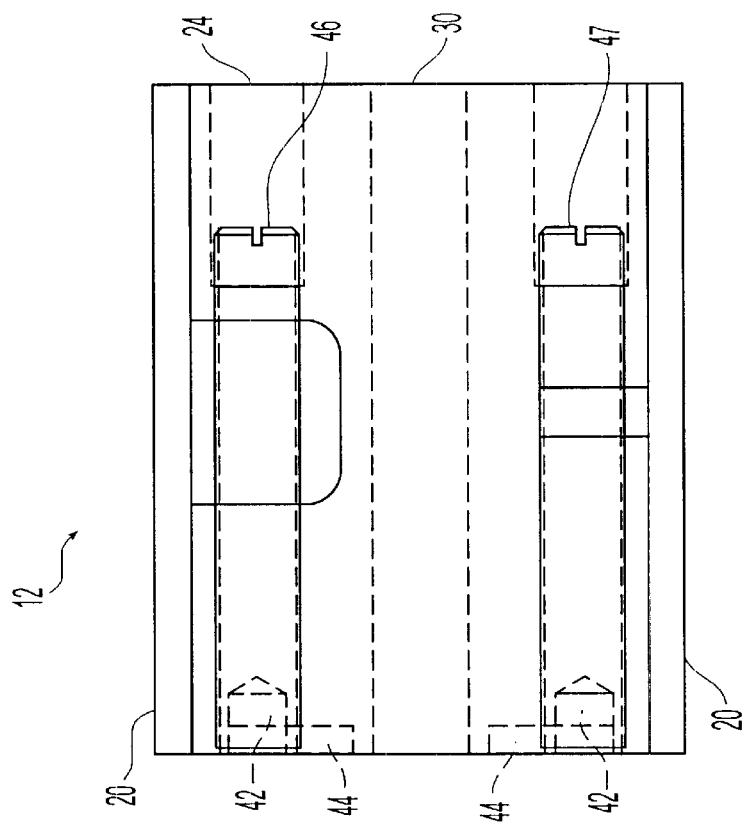
FIG. 6 is a top phantom view of the carriage member of FIG. 4.
Figure 5:
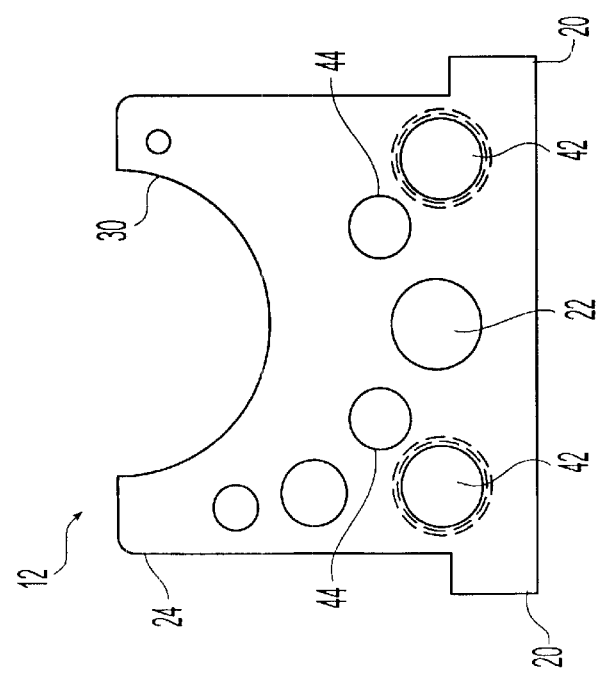
FIG. 5 is a front view of the carriage member of FIG. 4.

Referring now to FIGS. 4–6, body portion 24 includes a safety release mechanism for when carriage member 12 and drive member 16 are separate components. Specifically, when drive member 16 and carriage member 12 are coupled, drive member 16 via threaded shaft 34 provides the force to move carriage member 12. The safety mechanism allows drive member 16 to separate from carriage member 12 if the pulling force on the probe secured in carriage member 12 exceeds a threshold amount. As shown, the safety release member comprises a set of magnets 42, 43, 44, and 45 on body portion 24 that are operatively associated with a set of magnets on drive member 16, as described below. Other types of safety mechanisms are possible. For example, a frangible connection that breaks when a given force exceeds a preset amount can be used.

Regardless of the type of safety mechanism, the safety mechanism can be made adjustable so that the force at which carriage member 12 and drive member 16 uncouples is set by the user. For example, if a magnetic safety mechanism is used, the adjustable nature can be implemented by changing the magnetic field. Changing either the strength of the magnet or moving the magnet alters the magnetic field. If electromagnets are used, the strength of the field changes with voltage and/or current. If permanent magnets are used, some or all of the magnets can be changed.

As shown, all of the magnets are permanent, with magnets 44 and 45 fixed in location and magnets 42 and 43 adjustable in location. Thus, the force required to achieve separation of drive member 16 from carriage member 12 can be adjusted by moving the position of the two adjustable magnets 42 and 43. Located within body portion 24 are two screws 46 and 47 that are operatively associated with adjustable magnets 42 and 43. By rotating screws 46 and 47, adjustable magnets 42 and 43 can be moved either closer to the surface of body portion 24 thereby increasing the force required to separate drive member 16 from carriage member 12 or further inward toward the center of body portion 24 thereby decreasing the force required to separate drive member 16 and carriage member 12. In one embodiment, the separation force can be increased up to six lbs. and can be decreased down to three lbs. Although magnets 44 and 45 are shown as adjustable and magnets 42 and 43 are shown as fixed, magnets 42 and 43 can be adjustable while magnets 44 and 45 are fixed. In the alternative, the entire set of magnets can be adjustable or just one magnet out of the set of magnets can be adjustable.

Figure 7:
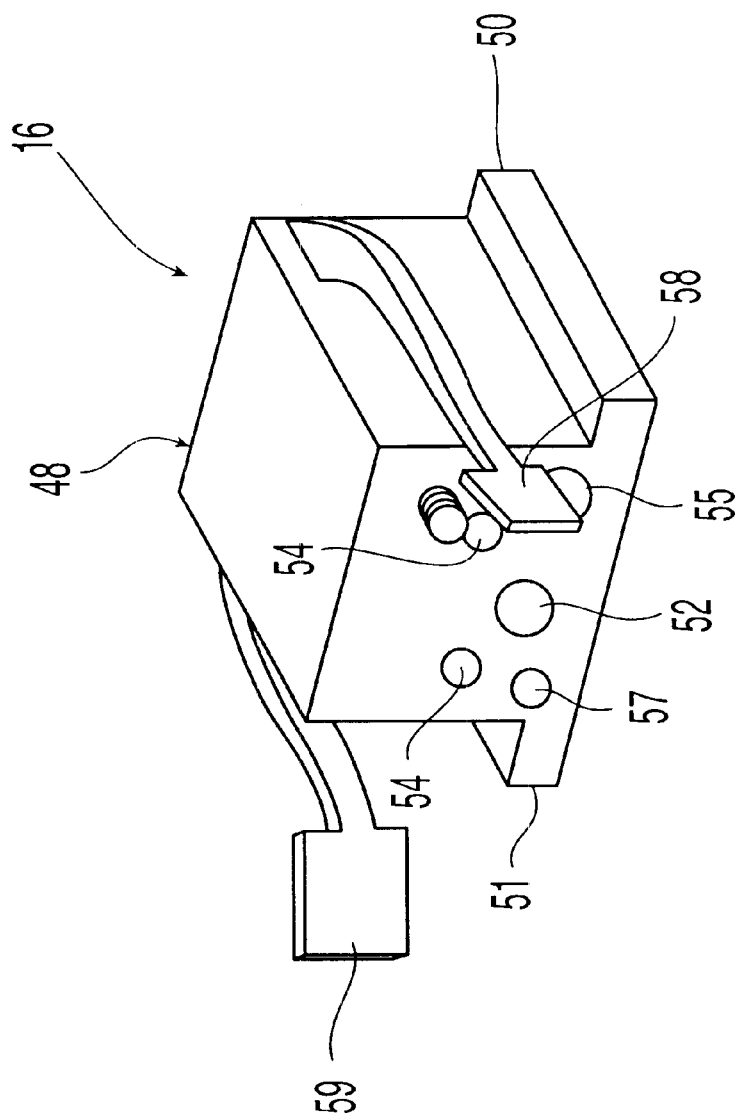
FIG. 7 is a perspective view of one embodiment of the drive member according to the present invention.
Figure 8:
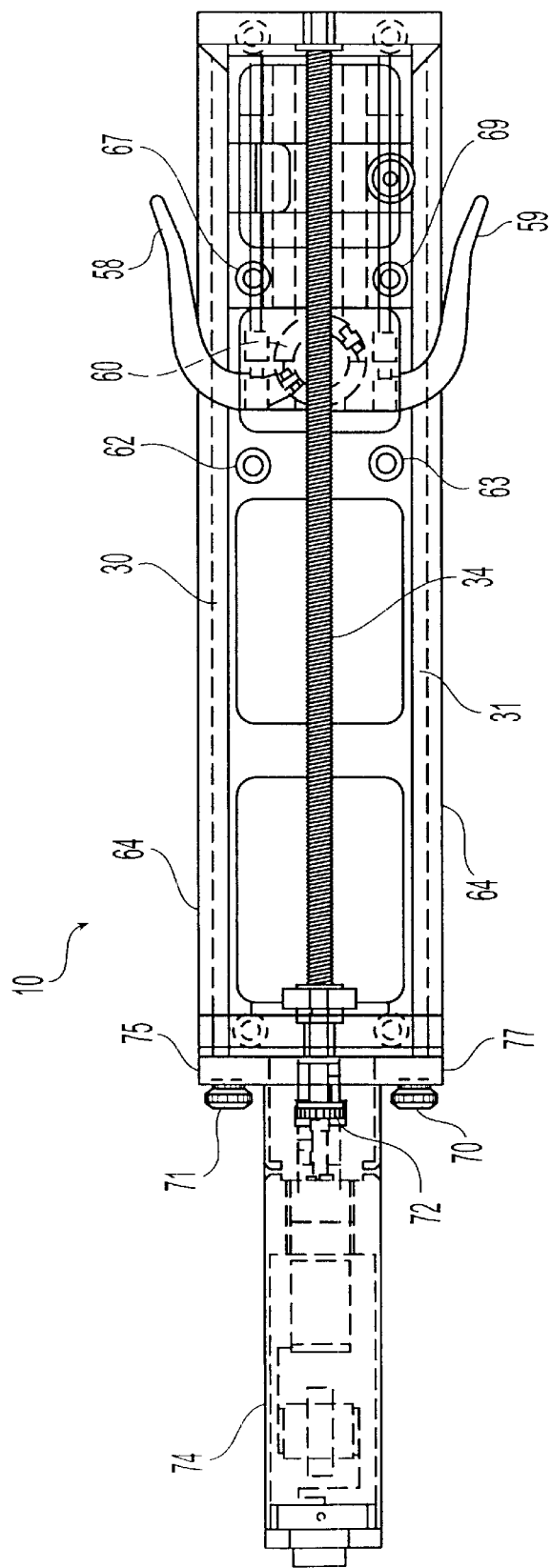
FIG. 8 is a top phantom view of the device of FIG. 1.

Referring now to FIGS. 7 and 8, drive member 16 is longitudinally moveable along base member 14. In an exemplary embodiment, drive member 16 has two parallel flanges 50 and 51 located at the base of drive member 16 that slideably fit within longitudinal slots 30 and 31 located within base member 14. Drive member 16 also has central bore 52 which is substantially cylindrical and has a first diameter that extends through the length of drive member 16. Threaded shaft 34 has a smaller second diameter and fits within central bore 52 allowing drive member 16 to slide along the length of base member 14 longitudinally if drive member 16 is disengaged from threaded shaft 34.

Drive member 16 comprises drive body portion 48 which houses central bore 52. Located at the base of drive body portion 48 are flanges 50 and 51 which extend outwardly in a transverse direction from the base of drive body portion 48 and run along the length of drive body portion 48. Drive body portion 48 also houses a set of magnets 53, 54, 55, and 57. Magnets 53, 54, 55, and 57 can be fixed in location or adjustable in location and are magnetically coupled with adjustable magnets 42 and 43 and fixed magnets 44 and 45 located within carriage member 12 thereby coupling carriage member 12 to drive member 16. In another embodiment, drive body portion 48 can house screws that are operatively associated with magnets 53, 54, 55, and 57 allowing the positioning of magnets 53, 54, 55, and 57 to be adjusted. In an exemplary embodiment, located on drive body portion 48 and extending transversely therefrom are drive member release levers 58 and 59.

Figure 9:
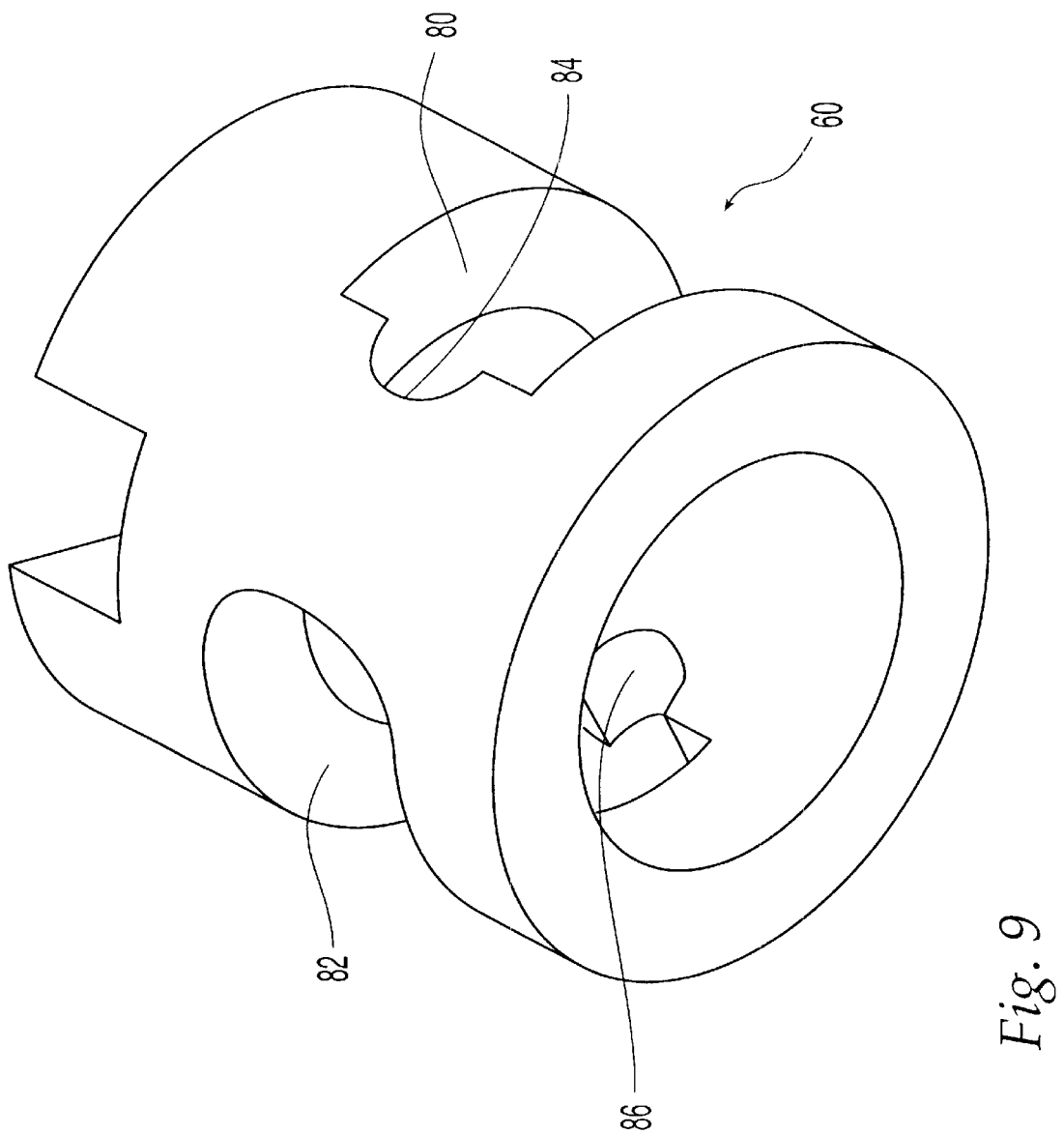
FIG. 9 is a perspective view of one embodiment of the engagement member according to the present invention.

Referring now to FIG. 9, in an exemplary embodiment, located within drive body portion 16 and attached to drive member release lever 58 is engagement member 60. Engagement member 60 may be circular and has two opposed elongated circular slots 80 and 82 located in the outside surface of engagement member 60. When drive member release lever 58 is not depressed, edges 84 and 86 of the elongated slots are engaged with the threads on threaded shaft 34. The engagement of drive member 16 with threaded shaft 34 allows drive member 16 to move horizontally in a controlled manner. Once drive member release lever 58 is depressed, engagement member 60 rotates slightly thereby disengaging the edges of the elongated circular slots from the threads of threaded shaft 34. Disengaging drive member 16 from threaded shaft 34 allows drive member 16 to move in a free sliding manner along the longitudinal direction. Therefore, depressing drive member release lever 58 disengages drive member 16 from threaded shaft 34, thereby permitting manual longitudinal positioning of drive member 16, and releasing drive member release lever 58 re-engages drive member 16 to threaded shaft 34, thereby permitting incremental longitudinal positioning of drive member 16.

Referring to FIGS. 2, 3, and 8, in an exemplary embodiment, base member 14 can include two opposed side rails 64 and 65 held in spaced relation by base 66 and transverse crossbars 68 and 70. Base 66 includes four holes 62, 63, 67, and 69 which can be used to secure base member 14 to a base plate and support stand (not shown). As described earlier, side rails 64 and 65 house longitudinal slots 30 and 31 and located in the middle of base member 14 is threaded shaft 34. Threaded shaft 34 is rotatably connected to base member 14 via transverse crossbars 68 and 70.

In one embodiment, located at one end of base member 14 are motor drive attachment elements 70 and 71 and motor engagement member 72. Motor engagement member 72 attaches to motor 74 at one end and attaches to threaded shaft 34 at the other end. If an electric motor is used, motor engagement member 72 can be made of any non-conductive material to electrically isolate the device 10 from motor 74. Motor 74 can be provided with two flanges 75 and 77 that interface with motor drive attachment elements 70 and 71, thereby allowing motor 74 to be removably attached to base member 14 and motor engagement member 72. Motor 74 supplies the power to turn motor engagement member 72 and threaded shaft 34. In one embodiment, motor 74 is a class 1, type B motor and is powered by a 6–12 V DC input.

The use of the device will now be further described using a transrectal ultrasound probe as an example. In an exemplary use, a probe is first secured to carriage member 12 and carriage member 12 is magnetically couple to drive member 16. Drive member release lever 58 is then depressed, disengaging drive member 16 from threaded shaft 34 allowing the user or physician to longitudinally slide drive member 16 and carriage member 12 along base member 14 until the desired position for the probe is reached. Once the desired position is obtained, drive member release lever 58 is then released engaging drive member 16 with the threads on threaded shaft 34. Via motor 74, threaded shaft 34 is rotated adjusting the position of carriage member 12 and drive member 16 incrementally.

The present invention provides probe support with a positioning function for precision axial longitudinal movement and rotation of a probe. During a procedure, such as brachytherapy or cryotherapy, the ultrasound probe is manually inserted into the rectum and, once the desired orientation is achieved as viewed and confirmed by the monitored ultrasound images, the probe is connected to the positioner (which is typically attached to a support stand). Alternatively, if the support stand has suitable mobility, the positioner and probe can be attached to the support stand before insertion into the rectum. With the support stand set in a fixed mode, a range of positively controlled microadjustments available with some support stands may be used to achieve an ideal probe or instrument orientation for starting the procedure.

The positioning function allows precise, independent, and reproducible longitudinal movement of the ultrasound probe while keeping it in accurate radial position. With a satisfactory starting image obtained, the positioner is used to guide the ultrasound probe and obtain transverse step section images. Direct ultrasound visualization is achieved by utilizing the available movements of the positioner.

The device has many advantages compared to the prior art. For example, the present invention has a quick and easy method for the operator to manually engage and disengage the carriage that holds the probe from the positioner. After initial placement and stabilization of the probe, this manual release is very useful for positioning the probe at a desired starting position quickly and safely and for performing repeat scans. It allows a quick manual advancing or positioning of the probe now locked into the carriage member within the patient's body at any desired point along a linear path without activating the positioner. Once so positioned, the positioner may be activated at any time to perform the pull-back of the carriage member and probe.

Another improvement is the safety release mechanism that prevents excessive pull-back force from being applied to the probe within the body by the positioner. Safety on insertion is assured by allowing manual insertion only. This gives normal tactile feedback to the operator. During withdrawal, this tactile feedback is absent and there is the risk of injury if excess force is applied. One way to achieve a safety release mechanism is to separate the carriage that holds the probe into two parts. The carriage part holds the transducer and the drive part engages the positioner. A release mechanism that allows these two parts to separate when excess force is applied during withdrawal of the probe can then be introduced.

Yet another improvement is providing complete electrical isolation of a drive motor and other electronic components from the operator, the patient, and the positioner. This is in addition to easy mechanical separation of the motor from the body of the positioner. This can be accomplished by the use of a non-conductive coupling device between the motor and the positioner, as well as a non-conductive motor assembly housing.

It is to be understood that the invention is not to be limited to the exact configuration as illustrated and described herein. For example, it should be apparent that a variety of medical instruments other than an ultrasound transducer probe would be suitable for use with the device according to the Detailed Description of the Invention. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A medical instrument positioning device comprising:
   a base member having a base and a central shaft operatively associated with the base;
   a carriage member (a) having a cavity configured and dimensioned to non-rotatably secure at least a portion of a medical instrument with respect to the carriage member and (b) slideably connected to the central shaft;
   a drive member coupled to the carriage member and engageable with the central shaft for controlled movement dependent on the central shaft and disengageable from the central shaft for sliding movement independent of and with respect to the central shaft; and
   a quick release member operatively associated with the drive member and having an inactive configuration in which the drive member engages the central shaft for controlled movement of the carriage member and drive member and an active configuration in which the drive member disengages the central shaft for independent sliding movement of the carriage member and drive member.

2. The device of claim 1 wherein the base further comprises:
   first and second crossbars; and
   first and second elongated, spaced parallel side rails, with the first and second side rails parallel with the central shaft.

3. The device of claim 2 wherein the base has a coupler for connection to a support stand.

4. The device of claim 2 wherein the central shaft is threaded and rotatably connected at first and second ends thereof to the first and second crossbars, and wherein rotation of the central shaft with the quick release member in the inactive configuration causes incremental movement of the drive member along the central shaft.

5. The device of claim 4 wherein at least one of the drive member and carriage member includes first and second flanges extending therefrom and the first and second side rails each include a slot for slideably receiving one of the flanges.

6. The device of claim 4 wherein the drive member further comprises an engagement member and wherein the quick release member comprises a release lever operatively associated with the engagement member, the engagement member configured and dimensioned to receive at least a portion of the release lever and upon actuation of the release member the engagement member either engages or disengages the central shaft.

7. The device of claim 1 wherein the carriage member further comprises a probe securing member to support the medical instrument and a fastener, wherein the probe securing member and fastener secure the medical instrument in the cavity of the carriage member.

8. The device of claim 1 further comprising a safety release element that uncouples the drive member from the carriage member when a movement force on the carriage member exceeds a threshold value.

9. The device of claim 8 wherein the safety release element comprises a magnet on the carriage member and a magnet on the drive member, the magnets magnetically coupling the drive member and the carriage member.

10. The device of claim 9 wherein the magnetic field of one of the magnets is adjustable to adjust the threshold value.

11. The device of claim 10 wherein the adjustable magnet is movable with respect to the other magnet to thereby adjust the threshold value.

12. The device of claim 11 further comprising a set screw for moving the adjustable magnet.

13. The device of claim 11 wherein the adjustable magnet is located on the carriage member.

14. The device of claim 1 wherein the base member includes at least one scale to provide indicia of displacement of the carriage member along the base member.

15. The device of claim 14 wherein the carriage member further comprises a carriage scale marker to indicate the numerical position of the carriage member on the base member.

16. The device of claim 1 wherein the base member further comprises a rotatable motor engagement member attached at a first end to the central shaft and removably coupled to a motor at a second end.

17. The device of claim 16 wherein at least a portion of the motor engagement member is made of a non-conductive material to electrically isolate the motor and the device.

18. A medical instrument positioning device comprising:
    a base member having a base and a central shaft operatively associated with the base;
    a carriage member having a cavity configured and dimensioned to receive at least a portion of a medical instrument and slideably connected to the central shaft;
    a drive member removably coupled to the carriage member and engageable with the central shaft for movement along the central shaft; and
    a safety release element that uncouples the drive member from the carriage member when a movement force on the carriage member exceeds a threshold value.

19. The device of claim 18 wherein the safety release element comprises a first plurality of magnets on the carriage member and a second plurality of magnets on the drive member, the first and second plurality of magnets magnetically coupling the drive member and the carriage member.

20. The device of claim 19 wherein the magnetic fields of at least some of the first and second plurality of magnets are adjustable to adjust the threshold value.

21. The medical instrument positioning device of claim 1, wherein the cavity of the carriage member is configured longitudinally with respect to the carriage member and is configured to receive at least the portion of the instrument laterally therein.

22. The medical instrument positioning device of claim 18, wherein the cavity of the carriage member is configured longitudinally with respect to the carriage member and is configured to receive at least the portion of the instrument laterally therein.

23. A medical instrument positioning device comprising:
    a base member having a base and a central shaft operatively associated with the base;
    a carriage member (a) comprising a longitudinal cavity configured and dimensioned to laterally receive at least a portion of a medical instrument and (b) translatable with respect to the central shaft;
    a drive member operable to translate the carriage member with respect to the central shaft, the drive member being engageable with the central shaft for controlled movement dependent on the central shaft and disengageable from the central shaft for translational movement independent of the central shaft; and
    a quick release member operatively associated with the drive member and having an inactive configuration in which the drive member engages the central shaft for controlled movement of the drive member and an active configuration in which the drive member disengages the central shaft for translation of the drive member independent of the central shaft.

* * * * *